United States Patent

Malewicz et al.

[11] Patent Number: 5,437,619
[45] Date of Patent: Aug. 1, 1995

[54] RANGE-OF-MOTION SPLINT WITH ECCENTRIC SPRING

[75] Inventors: Andrzej Malewicz, Minneapolis; Yuri Belman, Plymouth, both of Minn.

[73] Assignee: Empi, Inc., St. Paul, Minn.

[21] Appl. No.: 205,837

[22] Filed: Mar. 4, 1994

Related U.S. Application Data

[63] Continuation-in-part of Ser. No. 85,758, Jun. 30, 1993.

[51] Int. Cl.$^6$ .................................................. A61F 5/00
[52] U.S. Cl. ........................................ 602/20; 602/5; 602/16; 602/23; 602/26; 623/20
[58] Field of Search .................. 602/5, 16, 20, 23, 26; 623/18, 20, 39, 20; 482/127, 136

[56] References Cited

U.S. PATENT DOCUMENTS

| | | |
|---|---|---|
| 42,799 | 5/1864 | Shepard . |
| 1,847,823 | 1/1932 | Dresser . |
| 1,851,241 | 3/1932 | Dresser . |
| 2,395,768 | 7/1943 | Svoboda . |
| 2,413,634 | 12/1946 | Kolarik . |
| 2,646,793 | 7/1953 | Swiech et al. . |
| 2,675,578 | 4/1954 | Atwood et al. . |
| 2,797,431 | 7/1957 | Loria . |
| 2,934,785 | 5/1960 | Heuer . |
| 3,086,521 | 4/1963 | Desai et al. . |
| 4,180,870 | 1/1980 | Radulovic et al. . |
| 4,252,111 | 2/1981 | Chao et al. . |
| 4,397,308 | 8/1983 | Hepburn . |
| 4,433,679 | 2/1984 | Mauldin et al. . |
| 4,456,002 | 6/1984 | Barber et al. . |
| 4,485,808 | 12/1984 | Hepburn . |
| 4,489,718 | 12/1984 | Martin . |
| 4,493,316 | 1/1985 | Reed et al. . |
| 4,508,111 | 4/1985 | Hepburn . |
| 4,520,804 | 6/1985 | DiGeorge .................... 602/26 X |
| 4,538,600 | 9/1985 | Hepburn . |
| 4,565,190 | 1/1986 | Pirmantgen et al. ............... 602/26 |
| 4,602,620 | 7/1986 | Marx . |
| 4,624,246 | 11/1986 | Ajemian . |
| 4,633,867 | 1/1987 | Kausek et al. . |
| 4,643,177 | 2/1987 | Sheppard et al. . |
| 4,657,000 | 4/1987 | Hepburn . |
| 4,719,906 | 1/1988 | DeProspero . |
| 4,726,361 | 2/1988 | Farley . |
| 4,729,254 | 3/1988 | Nogami et al. . |
| 4,738,252 | 4/1988 | Friddle et al. . |
| 4,790,301 | 12/1988 | Silfverskiold . |
| 4,817,588 | 4/1989 | Bledsoe . |
| 4,844,057 | 7/1989 | Hoy . |
| 4,862,878 | 5/1989 | Davison et al. . |

(List continued on next page.)

FOREIGN PATENT DOCUMENTS 1426-580-A 9/1988 U.S.S.R. ................................. 602/20

Primary Examiner—Richard J. Apley
Assistant Examiner—Kim M. Lee
Attorney, Agent, or Firm—Kinney & Lange

[57] ABSTRACT

A range-of-motion splint for applying relatively constant torque across a joint undergoing rehabilitative therapy. The splint includes a first brace section configured to engage a portion of a patient's body on a first side of a joint, and a second brace section configured to engage a portion of the body on a second side of the joint. A first arm extends from the first brace section and a second arm extends from the second brace section. The first and second arms are connected by a dual axis pivot mechanism for rotational motion about both a primary joint axis and a lateral axis generally perpendicular to the primary joint axis. A first spring-engaging mount is located on the first arm at a position spaced from the primary joint axis. A second spring-engaging mount is located on the second arm at a position spaced from the primary joint axis. An eccentrically mounted spiral spring has an inner end mounted to the first spring-engaging mount, and an outer end mounted to the second spring-engaging mount. The amount of torque between the brace sections can be adjusted by a torque adjusting mechanism which winds and unwinds the spring. An adjustable stop mechanism can be used to limit the range of rotational motion between the brace sections. The brace sections can be locked with respect to one another by a locking mechanism which engages and prevents movement of the brace sections.

20 Claims, 6 Drawing Sheets

U.S. PATENT DOCUMENTS

| | | |
|---|---|---|
| 4,865,024 | 9/1989 | Hensley et al. . |
| 4,873,967 | 10/1989 | Sutherland .............................. 602/26 |
| 4,947,835 | 8/1990 | Hepburn et al. . |
| 5,000,169 | 3/1991 | Swicegood et al. ................... 602/26 |
| 5,002,044 | 3/1991 | Carter . |
| 5,002,045 | 3/1991 | Spademan . |
| 5,025,782 | 1/1991 | Salerno ................................... 602/26 |
| 5,036,837 | 8/1991 | Mitchell et al. ................... 602/26 X |
| 5,052,379 | 10/1991 | Airy et al. . |
| 5,060,640 | 10/1991 | Rasmusson . |
| 5,063,917 | 11/1991 | Young et al. .......................... 602/26 |
| 5,167,612 | 12/1992 | Bonutti . |
| 5,242,379 | 9/1993 | Harris et al. ........................... 602/26 |
| 5,352,190 | 10/1994 | Fischer et al. ......................... 602/26 |

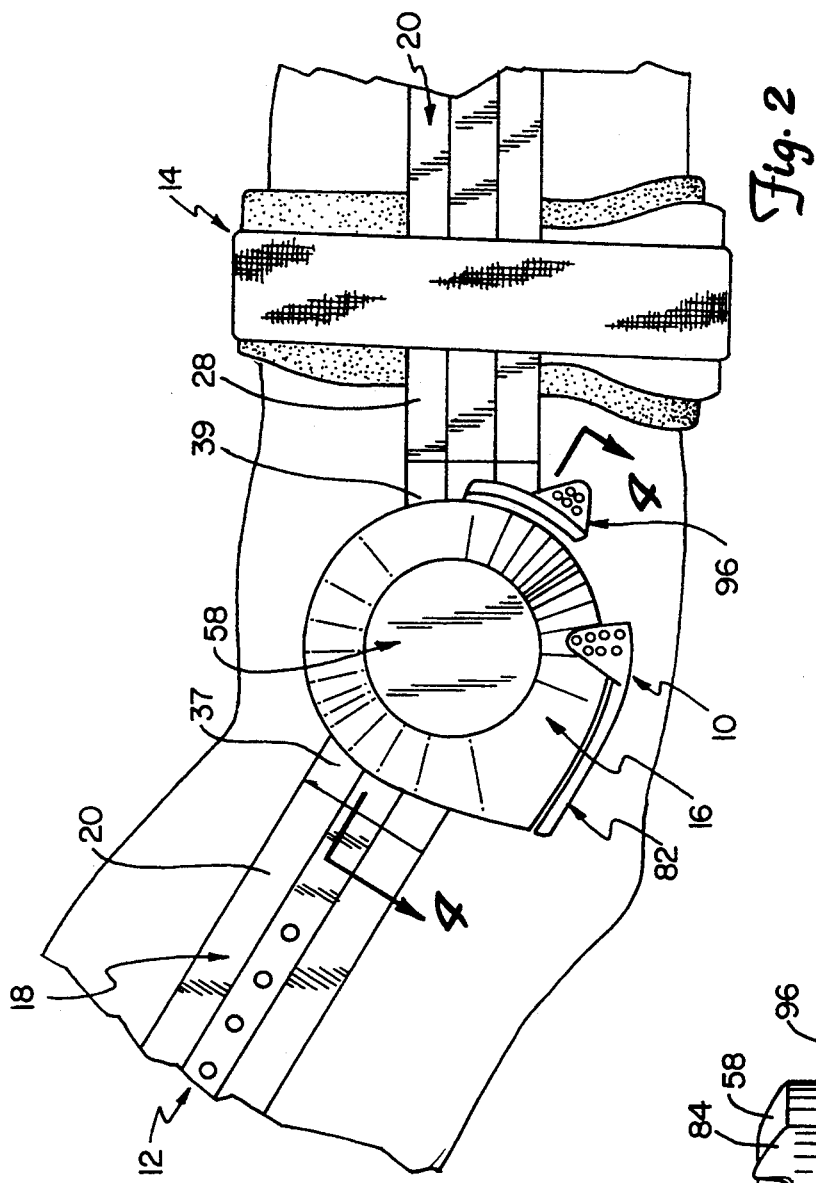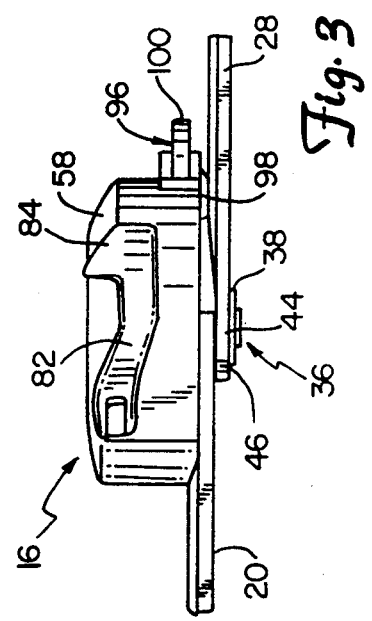

RANGE-OF-MOTION SPLINT WITH ECCENTRIC SPRING

REFERENCE TO RELATED APPLICATION

This application is a continuation-in-part of commonly assigned U.S. patent application Ser. No. 08/085,758, filed Jun. 30, 1993 and entitled Constant Torque Range-Of-Motion Splint.

BACKGROUND OF THE INVENTION

The present invention relates to dynamic splints or braces for applying torque across joints undergoing rehabilitative therapy.

Injuries or surgery to wrists, elbows, knees and other joints often results in flexion or extension contractures. These debilitating conditions prevent the patient from fully flexing (in the case of an extension contracture) or extending (in the case of a flexion contracture) the injured joint. Range-of-motion or ROM splints are dynamic devices commonly used during physical rehabilitative therapy to increase the range of motion over which the patient can flex or extend the joint. Splints of this type are known, and disclosed, for example, in the Mitchell et al. U.S. Pat. No. 5,036,837.

Commercially available range-of-motion splints typically include spring loaded brace sections for applying torque to the injured joint in opposition to the contracture. This force tends to gradually increase the working range or angle of joint motion. Springs, however, are passive devices and exert decreasing amounts of force as they retract. Most range-of-motion splints, therefore, require continual adjustment to maintain a constant amount of applied torque as the patient's range of joint motion increases during therapy. These torque adjusting procedures are time consuming and inconvenient.

It is evident that there is a continuing need for improved range-of-motion splints. In particular, there is a need for splints capable of applying relatively constant torque over the entire working joint angle range without adjustments. The amount of torque applied by the splint should also be adjustable to suit the needs of different patients. To be commercially viable, any such splint must be convenient to use and operate, and capable of being efficiently manufactured.

SUMMARY OF THE INVENTION

The present invention is a range-of-motion splint capable of applying relatively constant torque over the entire working range of a joint undergoing rehabilitative therapy. The splint includes first and second brace sections configured to engage portions of a patient's body on first and second sides of the joint, respectively, and a drive assembly. The first and second brace sections include first and second arms, respectively. A first pivot mechanism pivotally connects the first and second arms about a first splint pivot axis corresponding to a primary axis of joint motion. The drive mechanism includes a spiral spring having inner and outer ends for applying torque between the first and second brace sections. The spiral spring is eccentrically mounted to the first and second brace sections by an eccentric mount.

In one embodiment the eccentric mount includes first and second spring-engaging mounts. The first spring-engaging mount is located on the first arm at a position spaced from the first pivot axis. The second spring-engaging mount is located on the second arm at a position spaced from the first pivot axis. The inner end of the spring is mounted to the first spring-engaging mount, while the outer end of the spring is mounted to the second spring-engaging mount.

Another embodiment of the range-of-motion splint includes a second pivot mechanism for pivotally connecting the first and second arms for motion about a second pivot axis corresponding to a secondary axis of joint motion. The second pivot axis is perpendicular to, and intersects, the first pivot axis.

Yet another embodiment of the splint includes a locking mechanism for locking the rotational position of the first and second brace sections with respect to one another. The locking mechanism includes a cover mounted to the first arm for enclosing the spiral spring, and a rack on an interior surface of the cover. A pawl is pivotally mounted to the second arm for releasable engagement with the rack. The pawl is actuated by a lever which extends beyond the cover from the pawl.

BRIEF DESCRIPTION OF THE DRAWINGS

FIG. 2 is a detailed end view of the drive assembly and brace sections of the splint shown in FIG. 1.

FIG. 3 is a detailed side view of the drive assembly and brace sections of the splint shown in FIG. 1.

DETAILED DESCRIPTION OF THE PREFERRED EMBODIMENTS

Figure 1:
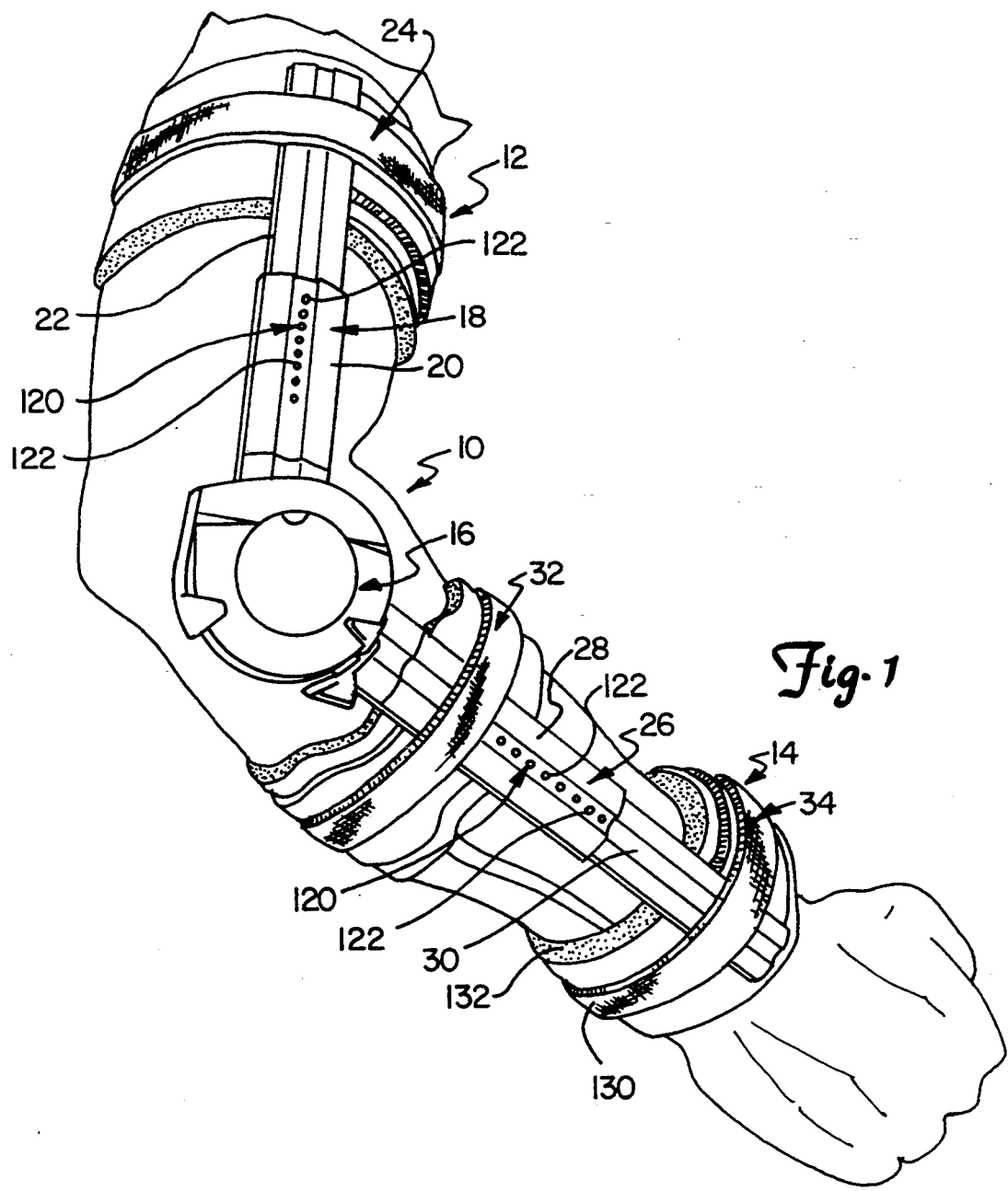
FIG. 1 is a perspective view of a range-of-motion splint in accordance with the present invention, shown in position on the arm of a patient.

A relatively constant torque, dynamic range-of-motion splint 10 in accordance with the present invention is illustrated generally in FIGS. 1 and 2. The illustrated embodiment of splint 10 is configured for rehabilitative elbow therapy and includes an upper arm-engaging brace section 12 (i.e., a first brace section for engaging a portion of the patient's body on a first side of the joint), a forearm-engaging brace section 14 (i.e., a second brace section for engaging a portion of the patient's body on the second side of the joint), and drive assembly 16. Brace section 12 includes an arm assembly 18 formed by rigid arm 20 and extendable arm 22, and an upper arm hook 24 mounted to the extendable arm. Similarly, brace section 14 includes an arm assembly 26 formed by rigid arm 28 and extendable arm 30, and forearm hooks 32 and 34. Forearm hook 32 is mounted to rigid arm 28, while hook 34 is mounted to extendable arm 30. Brace sections 12 and 14 and drive assembly 16 are interconnected by a dual-axis pivot assembly 36 which is shown in FIGS. 3–6. During use, splint 10 is mounted to the patient's arm and brace sections 12 and 14 adjusted to align pivot assembly 36 with the rotational axes of the patient's elbow. Drive assembly 16 provides relatively constant torque in opposition to contractures over the entire range of elbow motion, thereby alleviating the need for torque adjustments as the injury heals and the range of motion increases.

Pivot assembly 36 includes upper arm bracket 37, forearm bracket 39, and an elongated link 38 pivotally connected at one end to the upper arm bracket by pivot pin 40. Rigid arm 20 of brace section 12 is mounted to upper arm bracket 37 by screws or other fasteners (not shown), while rigid arm 28 of brace section 14 is similarly mounted to bracket 39. Pivot pin 40 defines a first or primary joint pivot axis about which brace sections 12 and 14 rotate. The end of bracket 39 interconnected to pivot assembly 36 is bifurcated and includes an elongated gap 42 forming a pair of extensions 44 on opposite sides of the bracket. The ends of extensions 44 are pivotally connected to the sides of link 38 by screws 46. Screws 46 define a second or lateral joint pivot axis which is perpendicular to the primary splint pivot axis. Gap 42 is sized to receive link 38 while allowing bracket 39 to pivot with respect to bracket 37 about the lateral joint pivot axis. Bracket 37 includes an extension 48 which extends beyond pivot pin 40 toward bracket 39 and is configured to engage pivot pin 70 of locking mechanism 90 (described below) to limit the range of rotational motion of brace sections 12 and 14. In the embodiment shown, extension 48 is located to limit the range of rotational motion between brace sections 12 and 14 to about minus ten degrees. The working range of splint 10 is between about minus ten degrees at full extension, and about one hundred and fifty degrees at full flexion.

Drive assembly 16 can be described with reference to FIGS. 4–8. As shown, drive assembly 16 includes a drive mechanism 56 mounted to brackets 37 and 39 and enclosed by cover 58. Drive mechanism 56 includes a spiral spring 60 having a first or inner end 62 and a second or outer end 68. Inner end 62 is mounted to a slot within the shaft 64 of gear 66. Outer end 68 is hooked to a pivot pin 70 extending from the end of link 38 opposite pivot pin 40. Gear 66 is rotatably mounted within cover 58 by a pin 72 which extends through gear shaft 64. The end of pin 72 adjacent gear 66 is mounted within a recess 74 on the interior surface of the face 59 of cover 58. The end of pin 72 adjacent shaft 64 is rotatably mounted within a recess or aperture in bracket 37. Cover 58 is fastened to bracket 37 by screws 63.

Spring 60 is eccentrically mounted with respect to the primary splint pivot axis formed by pin 40. As shown in FIGS. 5–8, the rotational axis of gear pivot pin 72 is offset or spaced from pivot pin 40. In the embodiment shown, when brackets 37 and 39 are linearly aligned, a line (not shown) extending through pins 72 and 40 forms a ninety degree angle with a line (also not shown) extending through pins 40 and 70. In other words, pins 70 and 72 form a right angle with respect to pivot pin 40. The offset between gear pivot pin 72 and pin 40 is one quarter inch (64 mm) in one embodiment. The functional characteristics of eccentrically mounted spring 60 are described below.

Figure 4:
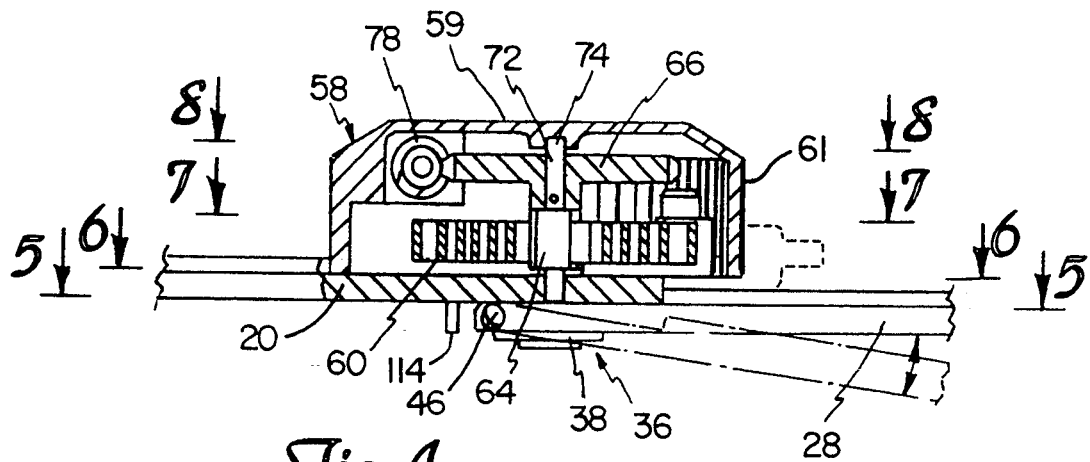
FIG. 4 is sectional side view of the drive assembly taken along line 4—4 in FIG. 2.
Figure 5:
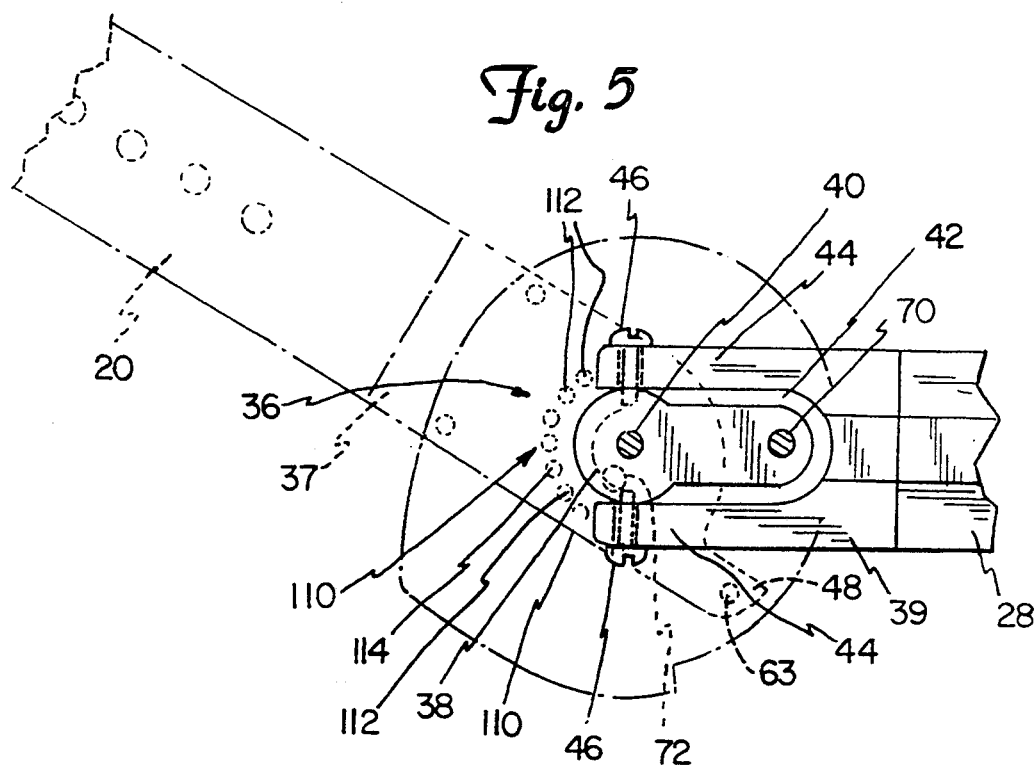
FIG. 5 is a detailed end view of the drive assembly taken along line 5—5 in FIG. 4, illustrating the pivot assembly.
Figure 6:
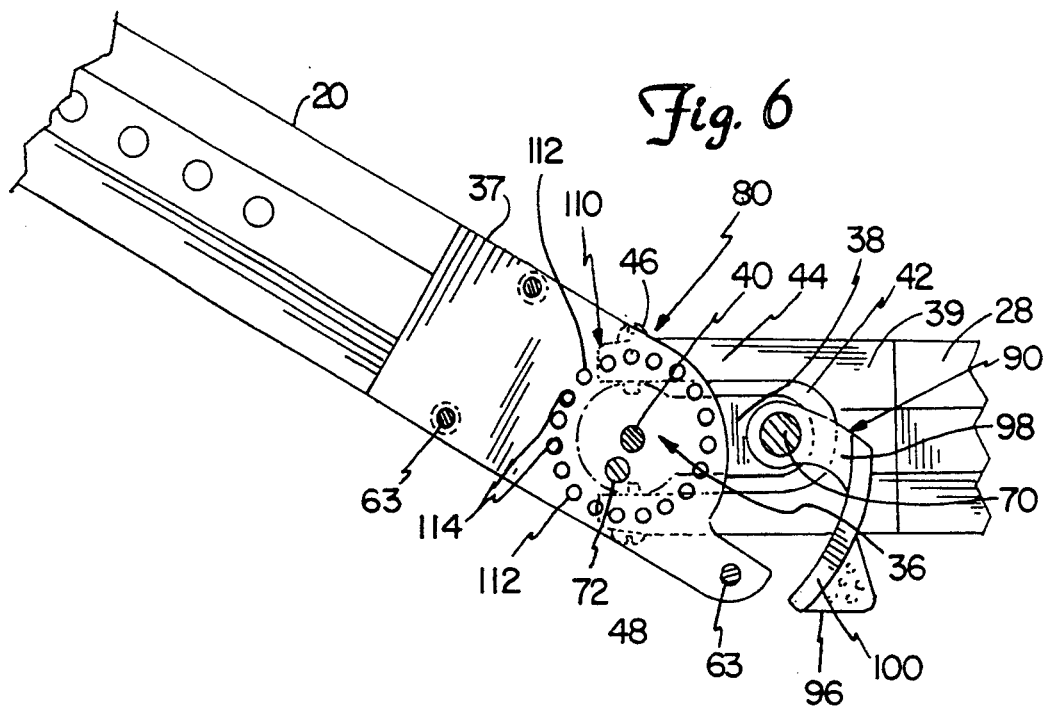
FIG. 6 is a detailed end view of the drive assembly taken along line 6—6 in FIG. 4, illustrating the pivot assembly.
Figure 8:
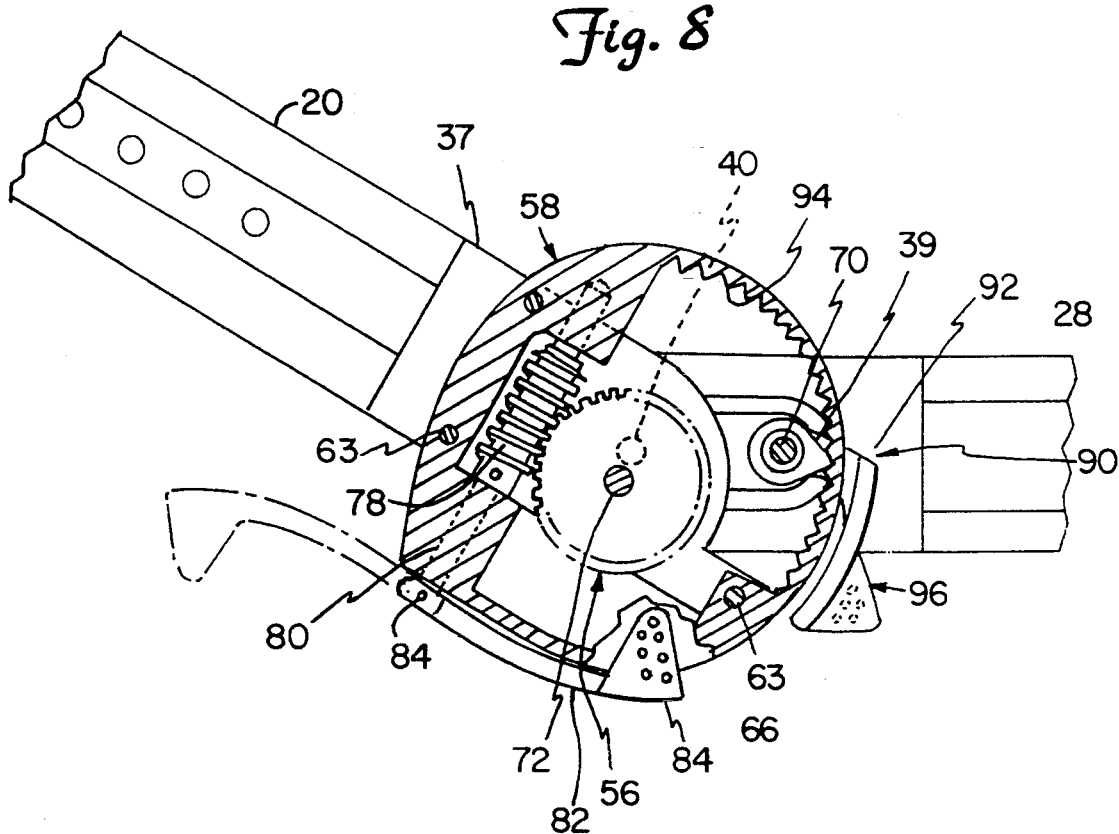
FIG. 8 is a detailed end view of the drive assembly taken along line 8—8 in FIG. 4, illustrating the torque adjusting mechanism.

As shown in FIGS. 4 and 8, an adjustment worm 78 is mounted within recesses in cover 58 for engagement with gear 66 and rotation about an axis perpendicular to pin 72. An end 80 of adjustment worm 78 extends through the cover side wall 61 and is connected to a crank 82 by pivot pin 84. Crank 82 is configured for pivotal movement between a retracted position adjacent to cover 58 (shown in solid lines), and an extended position (shown in broken lines). When in the extended position, the handle 84 of crank of 82 can be actuated to rotate adjustment worm 78, thereby rotating gear 66 to wind and unwind spiral spring 60 in order to increase and decrease the amount of torque applied across brace sections 12 and 14 by the spring. Gear 66, adjustment worm 78 and crank 82 thereby function as a torque adjusting mechanism.

Figure 7:
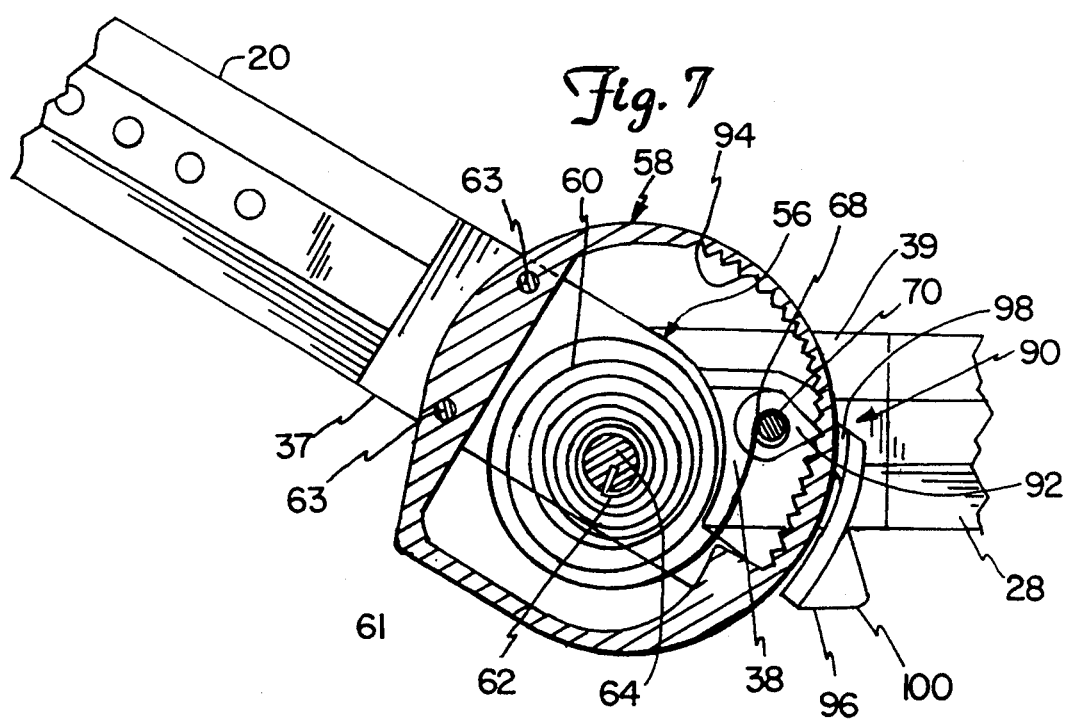
FIG. 7 is a detailed end view of the drive assembly taken along line 7—7 in FIG. 4, illustrating the spring and lock mechanism.

Locking mechanism 90 for releasably locking brace sections 12 and 14 with respect to one another can be described with reference to FIGS. 7 and 8. Locking mechanism 90 includes a pawl 92 pivotally mounted to pivot pin 70 and a rack 94 formed on the interior surface of cover side wall 61. Pawl 92 is actuated by a lever 96 which includes a base member 98 and handle 100. Base member 98 is mounted to pawl 70 and extends outwardly from case 58 between side wall 61 and bracket 39. Handle 100 extends from base member 98 and is positioned generally adjacent to the exterior of the cover side wall 61. Handle 100 is actuated to drive pawl 92 between a position disengaged from rack 94, and an over-center position engaged with the rack. When pawl 92 is in the disengaged position, brace sections 12 and 14 can freely rotate with respect to one another. When in the engaged position, pawl 92 is biased into engagement with rack 94 by the force of spring 60. Locking mechanism 90 enables brace sections 12 and 14 to be conveniently and rigidly locked with respect to one another at any desired position within the range of motion of splint 10. In one embodiment, the teeth forming rack 94 are symmetrical or bidirectional. Cover 58 can therefore be used on splints 10 configured for both flexion and extension contractures of joints on both the left and right sides of the patient's body by using different levers 96 that rotate in opposite directions.

An adjustable range-of-motion stop mechanism 110 enables a clinician to control the range of rotational motion between brace sections 12 and 14. As perhaps best shown in FIGS. 4–6, stop mechanism 110 includes threaded holes 112 circumferentially arranged around pivot pin 40 on the end of bracket 37, and a pair of removable pins 114 which can be threadedly engaged with the holes 112. Pins 114 extends from the side of bracket 37 facing bracket 39. The range of rotational motion between brace sections 12 and 14 is limited by the engagement of pins 114 with the ends of extensions 44 of bracket 39. A clinician can conveniently reposition one or both pins 114 within holes 112 to adjust the range of motion over which splint 10 can operate as the patient's condition improves.

Figure 9:
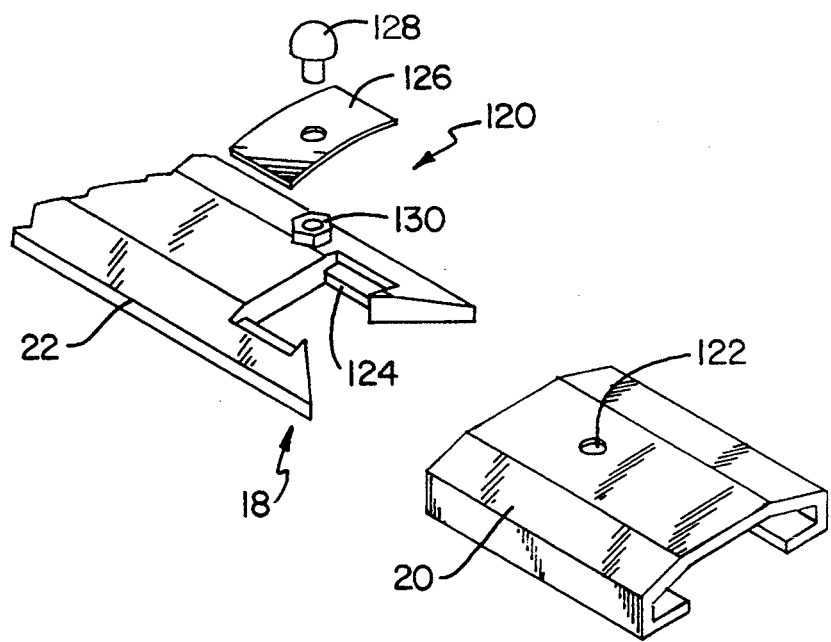
FIG. 9 is an exploded detailed view of the length adjusting mechanism of the brace sections.

Arm assemblies 18 and 26 each include a detent-type length adjustment mechanism 120 for adjustably positioning extendable arms 22 and 30 with respect to rigid arms 20 and 28, respectively. The length adjusting mechanism 120 on upper arm assembly 18, which can be identical to mechanism 120 on forearm assembly 26, is shown in detail in FIG. 9. As shown, rigid arm 20 is generally "C" shaped in cross section, and functions as track for slidably receiving extendable arm 22. A plurality of detent holes 122 extend through arm 20 and are aligned along the axis on which extendable arm 22 slides. The end of extendable arm 22 engaged with rigid arm 20 includes a recess 124 which is sized to receive a biasing member such as leaf spring 126. A detent button 128 is mounted to spring 126 by a rivet or other fastener 130. Button 128 is positioned to be linearly aligned with holes 122 as extendable arm 22 slides within rigid arm 20, and sized to engaged the holes. Spring 126 biases button 128 outwardly into a detent position engaged with holes 122. From the outer surface of rigid arm 20, a clinician can press button 128 into the arm to disengage extendable arm 22, and slide the extendable arm to a position appropriate for the patient. Button 128 can then be released to engage the nearest hole 122, thereby releasably locking the extendable arm 22 with respect to bracket 20.

Hooks 24, 32 and 34 are "C" shaped members, and have open sections (not visible in FIG. 1) enabling the hooks and splint to be mounted to and removed from the patient's arm. Forearm hook 34 includes a bendable "C" shaped foam covered aluminum member 130 rigidly mounted to extendable arm 30. A pad 132 of shape-retaining or "memory" foam is releasably secured to the inner surface of member 130 by hook and loop (e.g., Velcro brand) fasteners (not visible in FIG. 1). Hook 34 securely yet comfortably engages the patient's forearm, while foam pad 132 compensates for variations in the patient's limb structure. A strap 134 with hook and loop or other releasable fasteners (not visible in FIG. 1) is wrapped around hook 34 and the opening therein to securely engage the hook to the patient's forearm. Other than the size of the components, which are configured for differently sized sections of the patient's arm, hooks 24 and 32 can be structurally and functionally identical to hook 34 described above.

Figure 10:
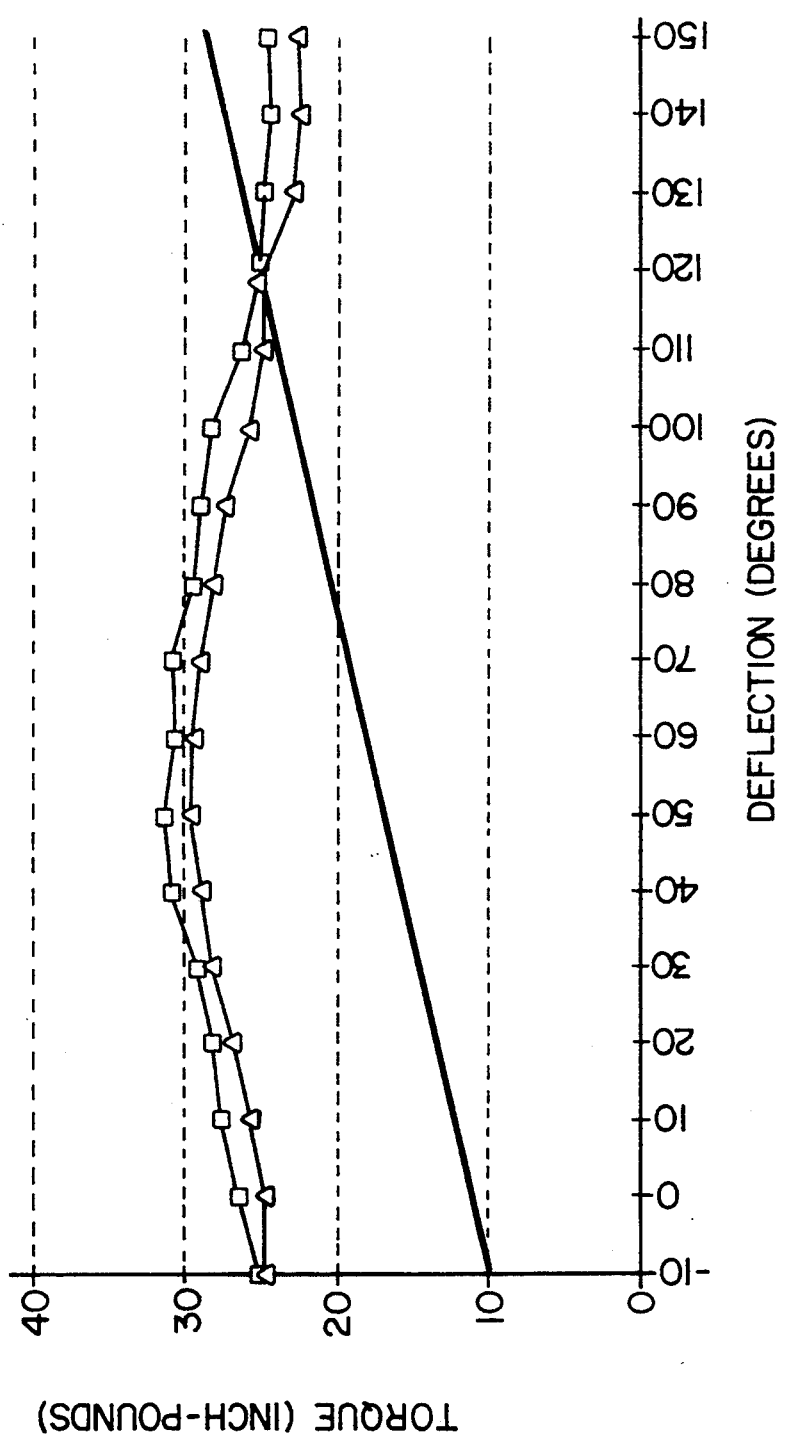
FIG. 10 is a graph of torque as a function of angular deflection for an eccentrically mounted spiral spring (data points shown by squares and triangles), and a concentrically mounted spring (shown by a solid line).

The relatively constant torque characteristics of eccentrically mounted spring 60 are illustrated in FIG. 10. FIG. 10 is a graph of the measured torque of a two inch spiral spring as a function of deflection when the inner end of the spring is spaced from the rotational axis of deflection by one quarter inch. Two sets of measured data for the same spring are shown, with the data points of one set represented by squares and the data points of the other set represented by triangles. For reference, the expected torque characteristics of the spring if it was concentrically mounted on the axis of deflection is shown by a solid line. From FIG. 10 it is evident that the amount of torque generated by the eccentrically mounted spring as a function of deflection is relatively constant with respect to that generated by a concentrically mounted spring.

Range-of-motion splint 10 offers considerable advantages over those shown in the prior art. The length adjusting mechanisms and replaceable hook pads enable the brace sections to be conveniently adjusted and fit to patients of varying size. The dual axis pivot mechanism allows the splint to accurately follow the natural motion of the patient's body. Relatively constant torque can be applied over the entire working range of the splint without the need for adjustments.

The amount of torque applied by the splint can be easily adjusted with the torque adjustment mechanism to accommodate the needs of different patients. The range of joint motion over which the splint operates can be conveniently adjusted with the stop mechanism. The use of the lock mechanism enables the patient to comfortably position and remove the splint. The splint can also be efficiently manufactured.

Although the present invention has been described with reference to preferred embodiments, those skilled in the art will recognize that changes can be made in form and detail without departing from the spirit and scope of the invention.

What is claimed is:

1. A range-of-motion splint for applying torque to a joint undergoing rehabilitative therapy, including:
   a first brace section configured to engage a portion of a body on a first side of a joint, the first brace section including a first arm;
   a second brace section configured to engage a portion of a body on a second side of a joint, the second brace section including a second arm;
   a first pivot mechanism for pivotally connecting the first and second arms about a first splint pivot axis corresponding to a primary axis of joint motion;
   a first spring-engaging mount on the first arm at a position spaced from the first pivot axis;
   a second spring-engaging mount on the second arm at a position spaced from the first pivot axis; and
   a spiral spring having an inner end and an outer end for applying torque between the first and second brace sections, the inner end mounted to the first spring-engaging mount on the first arm and the outer end mounted to the second spring-engaging mount on the second arm.

2. The range-of-motion splint of claim 1 and further including a torque adjusting mechanism for adjusting the torque applied by the spring between the first and second brace sections.

3. The range-of-motion splint of claim 2 wherein the torque adjusting mechanism includes:
   a gear rotatably mounted to the first arm at the position of the first spring-engaging mount, the inner end of the spring connected to the gear; and
   an adjustment worm rotatably mounted to the first arm and engaged with the gear, for rotating the gear to adjust the tension on the spiral spring.

4. The range-of-motion splint of claim 3 and further including:
   a cover mounted to the first-arm for enclosing the spiral spring and torque adjusting mechanism; and
   a handle mounted to the adjustment worm for movement between a retracted position adjacent to the cover and an extended position, for rotating the adjustment worm.

5. The range-of-motion splint of claim 4 and further including a locking mechanism mounted to the second arm, for releasably engaging the cover to lock the angular position of the first and second brace sections with respect to one another.

6. The range-of-motion splint of claim 5 wherein the locking mechanism includes:
   a rack on an interior surface of the cover;
   a pawl pivotally mounted to the second arm for releasable engagement with the rack; and
   a lever mounted to the pawl and extending from the cover, for actuating the pawl.

7. The range-of-motion splint of claim 1 and further including a locking mechanism for releasably locking the angular position of the first and second brace sections with respect to one another.

8. The range-of-motion splint of claim 7 wherein the locking mechanism includes:
   a cover mounted to the first arm for enclosing the spiral spring;
   a rack on an interior surface of the cover;

a pawl pivotally mounted to the second arm for releasable engagement with the rack; and a lever mounted to the pawl and extending from the cover, for actuating the pawl.

9. The range-of-motion splint of claim 1 and further including a second pivot mechanism for pivotally connecting the first and second arms for motion about a second pivot axis corresponding to a secondary axis of joint motion.

10. The range-of-motion splint of claim 9 wherein the second pivot mechanism includes a mechanism for pivotally connecting the first and second arms for motion about a second pivot axis which is perpendicular to the first pivot axis.

11. The range-of-motion splint of claim 10 where in the second pivot mechanism includes a mechanism for pivotally connecting the first and second arms for rotation about a second pivot axis which intersects the first pivot axis.

12. The range-of-motion splint of claim 1 wherein the first and second spring-engaging mounts are positioned to form about a ninety degree angle with the first splint pivot axis when the first and second brace sections are linearly aligned.

13. A range-of-motion splint for applying torque to a joint undergoing rehabilitative therapy, including;
a first brace section figured to engage a portion of a body on a first side of a joint, the first brace section including a first arm;
a second brace section figured to engage a portion of a body on a second side of a joint, the second brace section including a second arm;
a first pivot mechanism for pivotally connecting the first and second arms about a first splint pivot axis corresponding to a primary axis of joint motion;
a spiral spring having inner and outer ends, for applying torque between the first and second brace sections; and
an eccentric mount for eccentrically mounting the spiral spring with respect to the first splint pivot axis.

14. The range-of-motion splint of claim 13 wherein the eccentric mount includes:
a first spring-engaging mount on the first arm at a position spaced from the first pivot axis, the inner end of the spiral spring mounted to the first spring-engaging mount; and
a second spring-engaging mount on the second arm at a position spaced from the first pivot axis, the outer end of the spiral spring mounted to the second spring-engaging mount on the second arm.

15. The range-of-motion splint of claim 14 wherein the first and second spring-engaging mounts are positioned to form about a ninety degree angle with the first splint pivot axis when the first and second brace sections are linearly aligned.

16. A range-of-motion splint for applying torque to a joint undergoing rehabilitative therapy, including;
a first brace section configured to engage a portion of a body on a first side of a joint, the first brace section including a first arm;
a second brace section configured to engage a portion of a body on a second side of a joint, the second brace section including a second arm;
a first pivot mechanism for pivotally connecting the first and second arms about a first splint pivot axis corresponding to a primary axis of joint motion; and
a second pivot mechanism for pivotally connecting the first and second arms for motion about a second pivot axis corresponding to a secondary axis of joint motion.

17. The range-of-motion splint of claim 16 wherein the second pivot mechanism includes a mechanism for pivotally connecting the first and second arms for motion about a second pivot axis which is perpendicular to the first pivot axis.

18. The range-of-motion splint of claim 17 wherein the second pivot mechanism includes a mechanism for pivotally connecting the first and second arms for motion about a second pivot axis which intersects the first pivot axis.

19. The range-of-motion splint of claim 16 wherein:
the second arm has a bifurcated end forming two extensions;
the first pivot mechanism includes a link pivotally mounted to the first arm; and
the second pivot mechanism includes pins for pivotally mounting the extensions of the second arm to opposite sides of the link.

20. A range-of-motion splint for applying torque to a joint undergoing rehabilitative therapy, including:
a first brace section configured to engage a portion of a body on a first side of a joint, the first brace section including a first arm;
a second brace section configured to engage a portion of a body on a second side of a joint, the second brace section including a second arm;
a pivot mechanism for pivotally connecting the first and second arms about a splint pivot axis corresponding to a primary axis of joint motion; and
a spring connected to the first arm at a location spaced from the splint pivot axis and connected to the second arm at a location spaced from the splint pivot axis for applying torque between the first and second brace sections.

* * * * *

UNITED STATES PATENT AND TRADEMARK OFFICE
CERTIFICATE OF CORRECTION

PATENT NO. : 5,437,619

DATED : August 1, 1995

INVENTOR(S) : ANDRZEJ MALEWICZ, YURI BELMAN

It is certified that error appears in the above-indentified patent and that said Letters Patent is hereby corrected as shown below:

Col. 6, line 42, delete "-", between first and arm

Signed and Sealed this

Twenty-fourth Day of October, 1995

Attest:

BRUCE LEHMAN

*Attesting Officer*   *Commissioner of Patents and Trademarks*